United States Patent [19]

Itaoka et al.

[11] Patent Number: 5,019,040

[45] Date of Patent: May 28, 1991

[54] CATHETER

[75] Inventors: Toshinari Itaoka, Tokyo; Shinichi Hirata, Takarazuka, both of Japan

[73] Assignee: Koshin Sangyo Kabushiki Kaisha, Kobe, Japan

[21] Appl. No.: 402,905

[22] Filed: Aug. 31, 1989

[51] Int. Cl.$^5$ ..................... A61M 25/00; A61M 25/08
[52] U.S. Cl. ..................................... 604/95; 604/281; 604/20; 606/15
[58] Field of Search ............... 604/281, 95, 20; 606/7, 606/15

[56] References Cited

U.S. PATENT DOCUMENTS

| | | | |
|---|---|---|---|
| 4,411,655 | 10/1988 | Schreck | 604/165 |
| 4,531,943 | 7/1985 | Van Tassel et al. | |
| 4,551,292 | 11/1985 | Fletcher et al. | |
| 4,753,223 | 6/1988 | Bremer | 604/95 |
| 4,790,310 | 12/1988 | Ginsburg et al. | 606/7 |
| 4,799,474 | 1/1989 | Ueda | 604/281 |
| 4,838,246 | 6/1989 | Hahn et al. | 606/15 |
| 4,919,133 | 4/1990 | Chiang | 604/281 |
| 4,944,727 | 7/1990 | McCoy | 604/95 |
| 4,969,890 | 11/1990 | Sugita et al. | 606/192 |

FOREIGN PATENT DOCUMENTS 59-125759  1/1986  Japan .

OTHER PUBLICATIONS

Author: Koichi Ichikawa; The 61st Conference on Japanese Medical Instrumentation, Title: Improvement of Intraoperative Antegrade Coronary Angioscopy. Date: Apr. 1986, (2 documents—one is a supplement).

Author: The Furukawa Electric Co., Ltd., Tokyo, Japan: Title: Information Sheet of Laser Endoscopy for Blood Vessel, dated Feb., 1986.

Author: The Furukawa Electric Review No. 76, (has substantially the same content as document mentioned immediately above), dated Nov. 1985.

*Primary Examiner*—Richard J. Apley
*Assistant Examiner*—Lynne A. Reichard
*Attorney, Agent, or Firm*—Marshall, O'Toole, Gerstein, Murray & Bicknell

[57] ABSTRACT

A catheter comprising a tubular structure having a channel extending through it. A connector is attached to one end of the structure, and adapted to be connected to an energy source. Energy guide fibers extend through the connector and are embedded in the tubular structure, and are adapted to be connected to the energy source. The connector has at least one inlet port connected to the channel. A shaped memory alloy is woven with certain portions of the energy guide fibers on one side of the tubular structure.

7 Claims, 4 Drawing Sheets

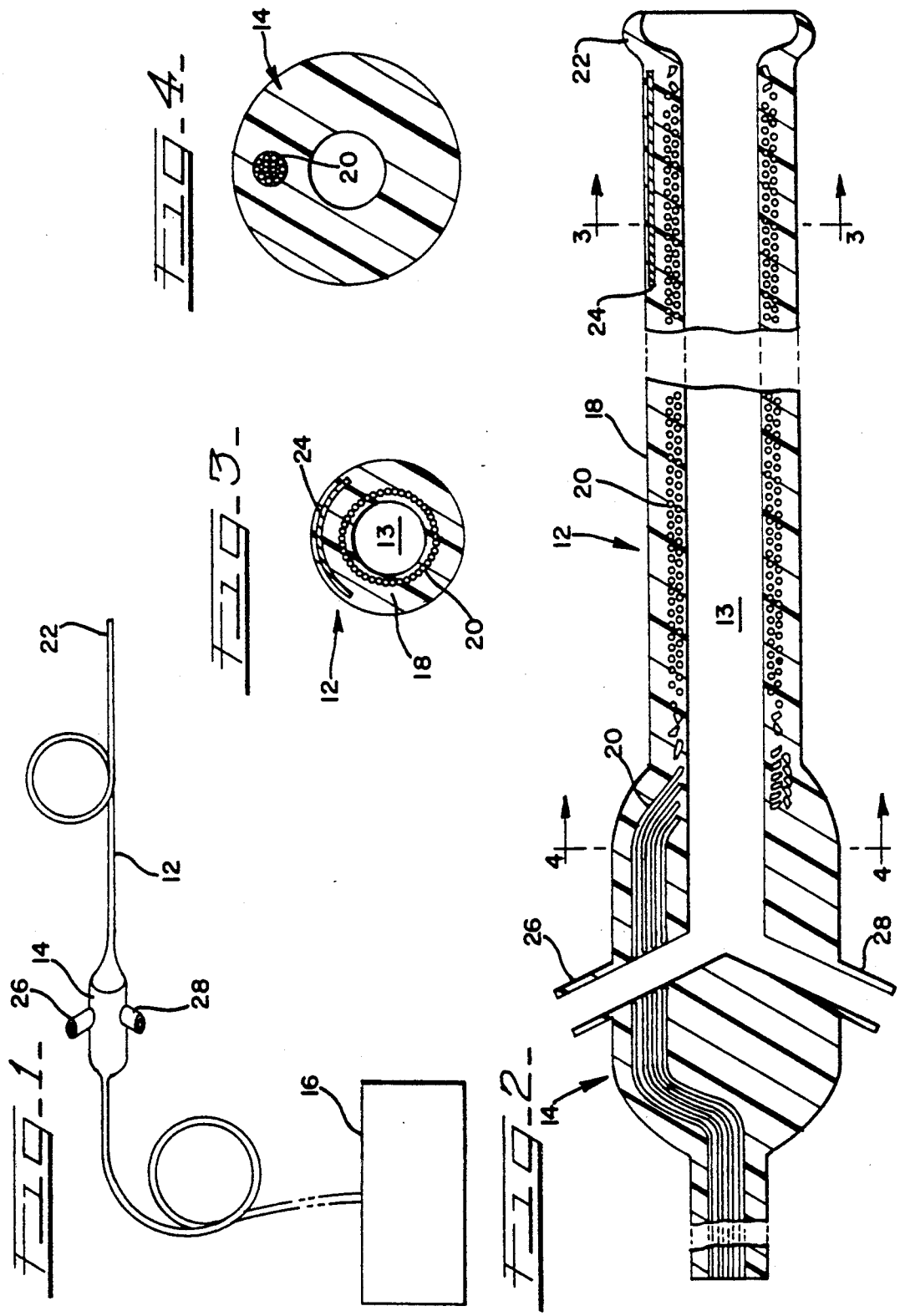

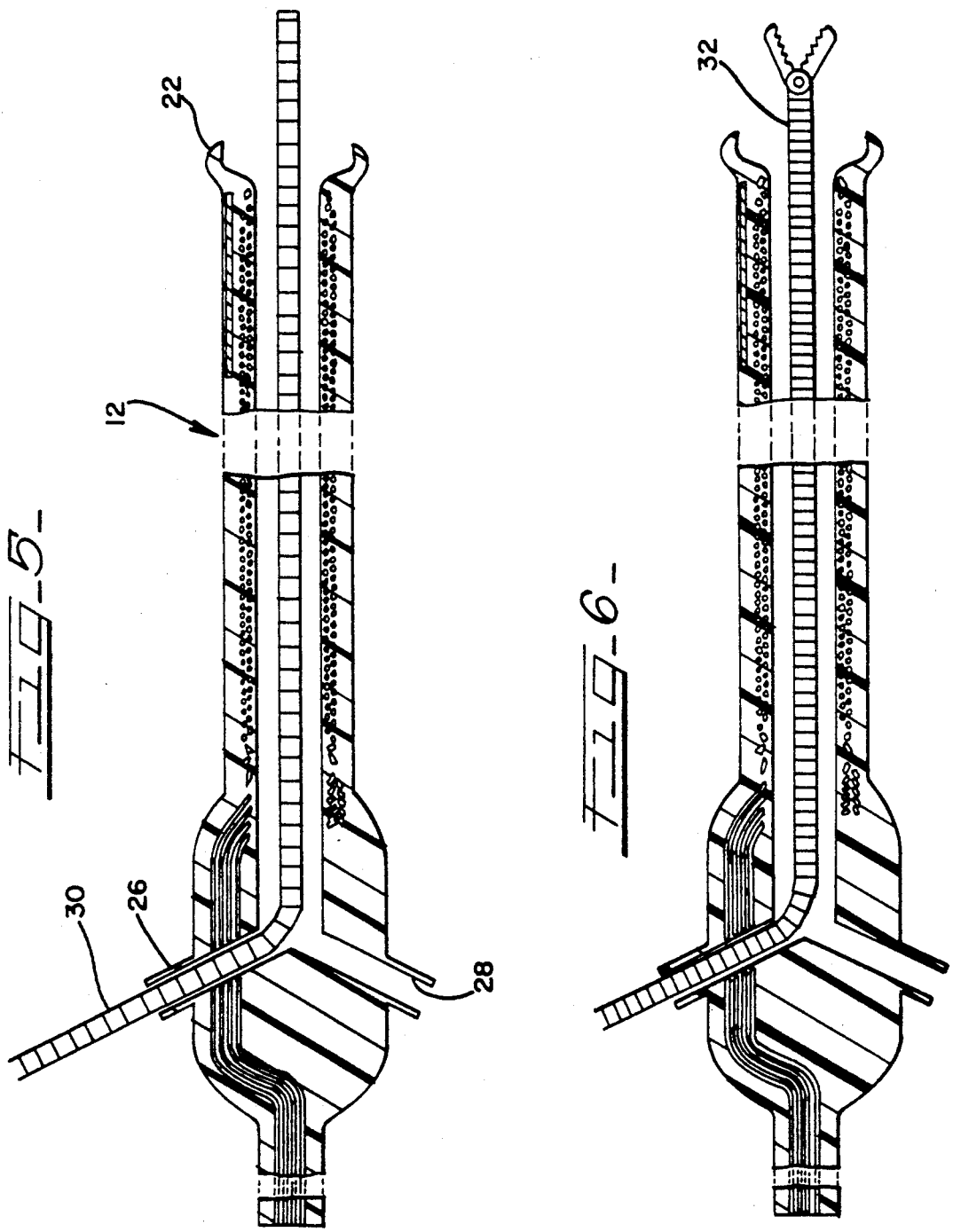

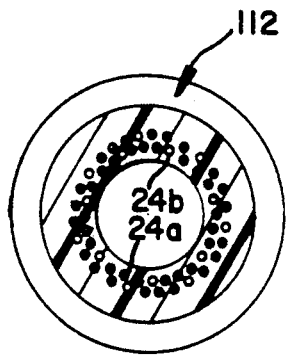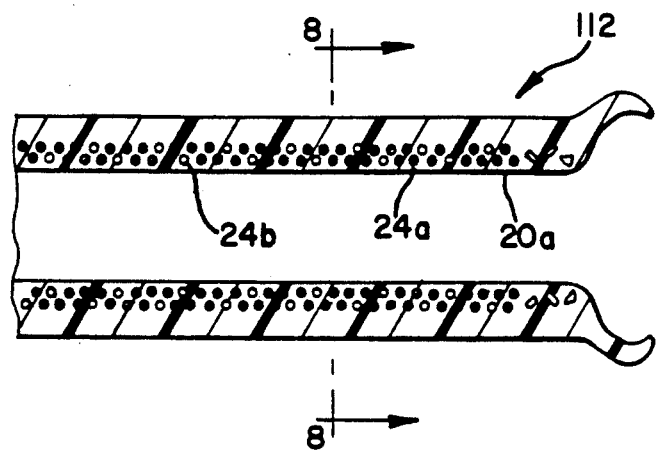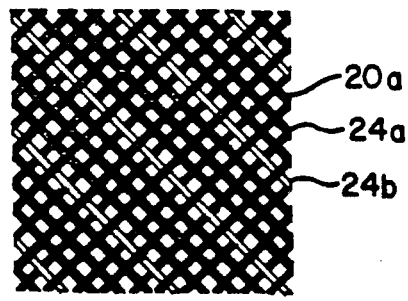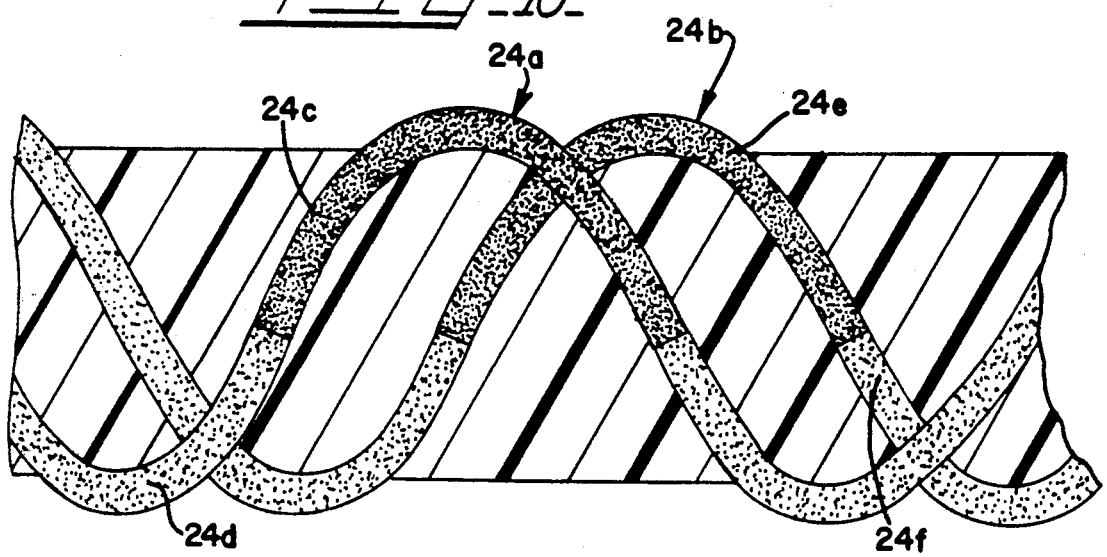

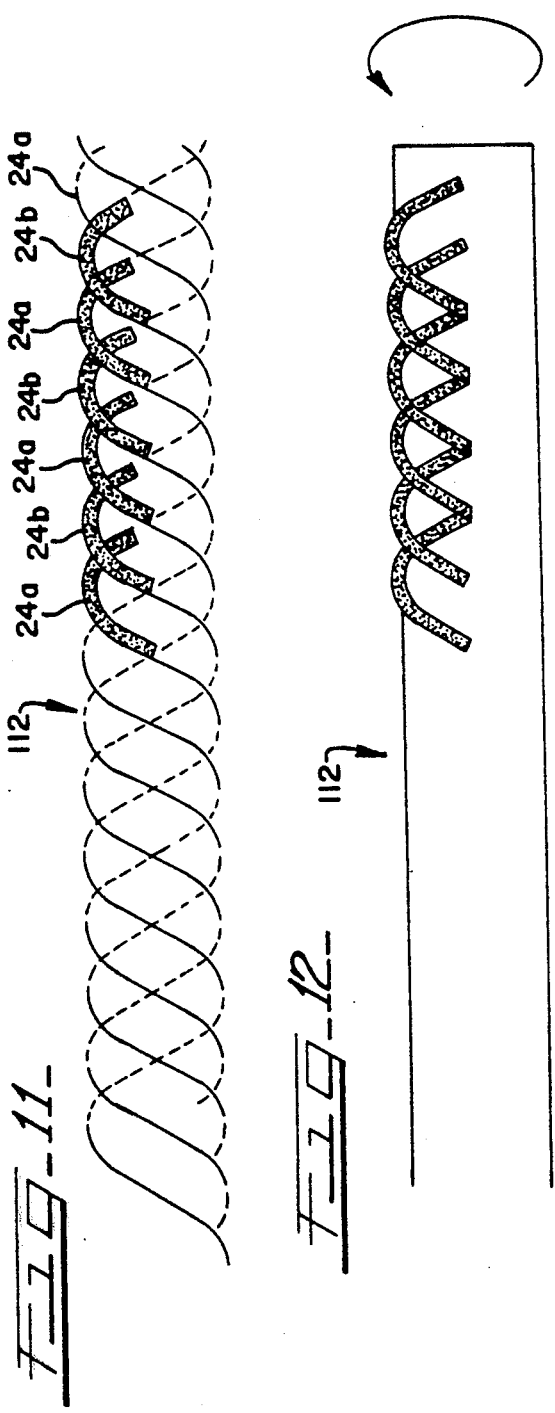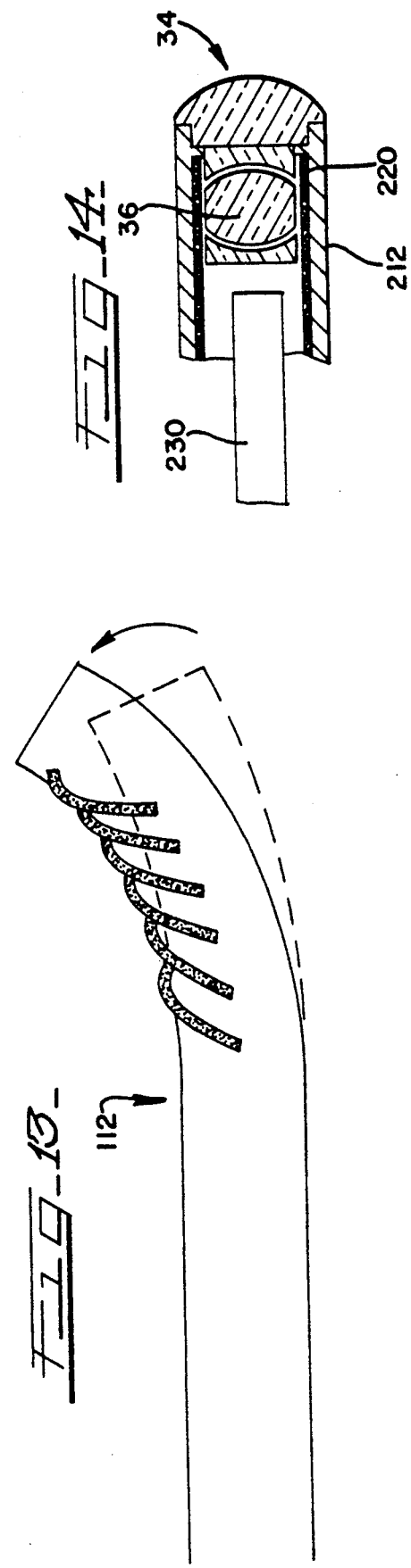

CATHETER

FIELD AND BACKGROUND OF THE INVENTION

This invention relates to a catheter for medical laser treatment, medical ultrasonic treatment, and medical examination by a fiberscope, etc., of small blood vessels and other small hollow organs of living organisms.

Conventional catheters of this type have a tubular structure including a bundle of fibers that transmit energy and a flexible fiber that can move inside the structure. These catheters can merely transmit energy, and need a separate fiberscope or the like for treatment or examination inside small hollow organs. The tubular structure must be guided or positioned in a living organ by a guide wire or the like.

U.S. Pat. No. 4,531,943 dated July 30, 1985 shows another catheter having a tubular structure with a soft plastic tip which, when pressed, can be deformed to increase the contact surface area.

SUMMARY OF THE INVENTION

It is a general object of the invention to provide a catheter for easy treatment or examination inside small hollow organs.

A catheter according to the invention comprises a tubular structure having a channel extending through it. A connector is attached to one end of the structure, and adapted to be connected to an energy source. Energy guide fibers extend through the connector and are embedded in the tubular structure, and are adapted to be connected to the energy source. The connector has an inlet port connected to the channel.

BRIEF DESCRIPTION OF THE DRAWINGS

Preferred embodiments of the invention are shown in the accompanying drawings, wherein FIG. 1 is a schematic side view of a catheter according to the invention;

FIG. 2 is an enlarged fragmentary view in longitudinal section of the catheter of FIG. 1;

FIG. 3 is a cross section taken along the line 3—3 of FIG. 2;

FIG. 4 is a cross section taken along the line 4—4 of FIG. 2;

FIGS. 5 and 6 are views similar to FIG. 2, showing different forms of use of the catheter;

FIG. 7 is a schematic fragmentary view in longitudinal section of another embodiment of the invention;

FIG. 8 is a cross section taken along the line 8—8 of FIG. 7;

FIG. 9 is an enlarged fragmentary view of mesh-like woven fibers embedded in the catheter wall;

FIGS. 10 to 13 are diagrammatic views further illustrating the structure and functioning of the embodiment shown in FIGS. 7 to 9; and FIG. 14 is a longitudinal section of a catheter tip according to the invention.

DETAILED DESCRIPTION OF THE INVENTION

With reference to FIG. 1, the catheter includes a tubular structure 12 attached to one end of a connector 14, the other end of which is connected to an energy (e.g. conventional optic light) source 16 With reference to FIGS. 2 and 3, the tube 12 forms an interior channel 13 which has a diameter of about 1-2 mm. The tube 12 is formed and/or coated by a soft flexible non-thrombogenic material 18 of a high molecular compound, such as silicone, which deters platelet coagulation.

The material 18 covers a number of energy (e.g. optic light, laser wave and ultrasonic energy) guide fibers 20 (FIG. 3) which are embedded in it and are woven in a tubular meshlike form. The material 18 terminates at the front end in an integral open tip 22 which is soft and transparent, and the energy guide fibers 20 extend to the tip 22. Also embedded in the material 18 is a sheet 24 of a shape-memory alloy (FIGS. 2 and 3) such as NiTi alloy adjacent the tip 22 for controlling angulation. The sheet 24 is an arcuate member which is outside the fibers 20 and extends along one side only of the tube 12. The sheet 24 has a predetermined shape at a specific temperature but changes its shape with temperature changes. Thus an increase or a decrease in the temperature of the sheet 24 will cause the tip 22 to flex up or down as seen in FIG. 2.

The connector 14 has two inlet ports 26 and 28 (see FIGS. 1 and 2) connected to the channel 13. The fibers 20 extend along the tube 12 and through the connector 14 (FIG. 4), and are connected to the energy source 16 (FIG. 1).

In use, the tip portion of tube 12 is inserted into a small hollow organ (not shown), and a vascular contrast medium or other solution is flowed from the inlet 28 and through the channel 13 and out of the tip 22, while the fibers 20 transmit light from the source 16 and out of the tip 22. The fibers 20 form an annular light (and/or another energy) path which extends forwardly from the front end of the tube 12.

At the same time, as shown in FIG. 5, an image fiber and/or a laser fiber 30 of a fiberscope and/or a laser irradiation unit (not shown) can be inserted through the other inlet 26 and into the tube 12 to project from the tip 22. This fiber 30 is used to examine an affected portion of the organ which is illuminated by the light and/or laser wave from the fibers 20, and/or treat it by irradiating a laser beam onto it and/or detection reflected laser wave from the end of fiber 30.

Instead, as shown in FIG. 6, a biopsy forceps 32 and/or an echo transmission fiber (not shown), for example, may be inserted through the inlet 26 to treat the organ.

A saline solution or other liquid may be supplied into the tube 13 from the inlet 28. The temperature of the liquid may be varied to heat or cool the shape memory alloy 24, which will, when its temperature is changed, be deformed and bend the front end 22 of tube 12 at an angle without necessitating a guide wire.

In FIGS. 7-13, light guide fibers 20a are interwoven with two types of shape-memory alloy strings 24a and 24b. With specific reference to FIGS. 11 and 12, a plurality of strings 24a and a plurality of strings 24b are provided alternately and are interwoven to form a tube 112. Each string 24a and 24b is formed of alternating equal length sections of a shape memory alloy and a non shape memory alloy. In FIGS. 10 and 11, the shape memory alloy section (which is darkened) of the string 24a is indicated by the numeral 24c and the non shape memory section is indicated by the numeral 24d; for the string 24b, these two sections are indicated by the numerals 24e and 24f. Further, the strings 24a and 24b are woven such that the shape memory alloy sections 24c and 24e are on one side of the tube 112, as illustrated in FIGS. 10 and 11. The two sections 24c and 24e may both be made of a shape-memory alloy (e.g. NiTi alloy but with different ratios of the amounts of Ni and Ti). Alternatively, the two sections 24c and 24e may be made of NiTi alloy with the same ratio of Ni and Ti but treated in a manner known to those skilled in the art to memorize different shapes. The strings 24d and 24b preferably have the sections 24c and 24e adjacent the tip 22 so that only the tip portion will bend with temperature changes. The two types or ratios act at different temperatures to bend the tube 112 at different angles as shown in FIG. 13, and the strings 24a and 24b also function as reinforcement.

In FIG. 14, the catheter includes a tube 212 with energy guide fibers 220 embedded in it. In the opening at the front end of the tube 212 is provided an optical system 34 including an object lens 36. An image fiber 230 extends into the tube 212 from a fiberscope (not shown) so that its front end faces closely behind the optical system 34. The image fiber 230 forms an image transmission path for image or wavelength analysis. This, of course, improves the examination capacity of the fiberscope.

What is claimed is:

1. A catheter comprising a tubular structure having a channel extending through it, a connector attached to one end of the structure and adapted to be connected to an energy source, the connector having at least one inlet port connected to the channel, energy guide fibers extending through the connector and along the tubular structure and adapted to be connected to the energy source, and a plurality of strings woven with said energy guide fibers and embedded in said tubular structure, said strings having portions on one side of said tubular structure which are formed of a shape memory alloy.

2. The catheter of claim 1, wherein said tubular structure comprises a material which covers said fibers and which is made of a high molecular compound for deterring platelet coagulation.

3. The catheter of claim 1, wherein said portions of said strings of shape memory alloy are of different types of shape memory alloy.

4. The catheter of claim 1, wherein said tubular structure has said shape memory alloy portions adjacent its front end.

5. The catheter of claim 1, wherein said energy guide fibers are quartz fiber, and said energy source is a light laser acoustic energy source or any combinations of thereof.

6. The catheter of claim 5, wherein the front end of said tubular structure is provided with an optical sensor having an object lens.

7. The catheter of claim 1, wherein said woven energy guide fibers and said strings form a tube.

* * * * *